United States Patent [19]

Kang et al.

[11] Patent Number: 5,433,896
[45] Date of Patent: Jul. 18, 1995

[54] DIBENZOPYRROMETHENEBORON DIFLUORIDE DYES

[75] Inventors: Hee C. Kang; Richard P. Haugland, both of Eugene, Oreg.

[73] Assignee: Molecular Probes, Inc., Eugene, Oreg.

[21] Appl. No.: 246,790

[22] Filed: May 20, 1994

[51] Int. Cl.[6] .................. C09K 3/00; C09K 11/06; C09K 11/02
[52] U.S. Cl. ................. 252/700; 252/301.16; 252/301.34; 252/301.35; 548/110; 548/405
[58] Field of Search .............. 252/700, 301.16, 301.17, 252/301.34, 301.35; 548/110, 405

[56] References Cited

U.S. PATENT DOCUMENTS

| 4,774,339 | 9/1988 | Haugland et al. | 548/405 |
| 4,916,711 | 4/1990 | Boyer et al. | |
| 5,187,288 | 2/1993 | Kang et al. | 548/110 |
| 5,248,782 | 9/1993 | Haugland et al. | 548/110 |
| 5,274,113 | 12/1993 | Kang et al. | 548/405 |
| 5,326,692 | 7/1994 | Brinkley et al. | |
| 5,338,854 | 8/1994 | Kang et al. | |

OTHER PUBLICATIONS

Maekawa et al., Chem. Ber. 101, 847 (1968).
Weygand et al., Chem Ber. 89, 1994 (1956).
Dierichs et al., Chem. Ber. 90, 1208 (1957).
Newman, J. Org. Chem. 26, 2630 (1961).
Kotali et al. Tet. Lett. 28, 4321 (1987).
Org. Synth. 2, 543.
Chemical Abstracts 79:126122r (1973) Svirevski et al.
Chemical Abstracts 82:72716d (1975) Minchev et al.
Haugland, Molecular Probes Handbook Of Fluorescent Probes and Research Chemicals Sets 1-11 (1992).

Primary Examiner—Philip Tucker
Attorney, Agent, or Firm—Allegra J. Helfenstein; Anton E. Skaugset

[57] ABSTRACT

The invention relates to fluorescent dyes that are substituted or unsubstituted derivatives of 1-[isoindolyl]-methylene-isoindole that are bound through both isoindole nitrogens to a boron difluoride moiety, forming a fluorescent dibenzopyrromethenboron difluoride compound

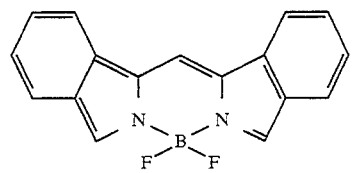

whose fluorescence properties are modified by the selection of appropriate chemical substituents.

The dibenzopyrromethenboron difluoride compound is optionally substituted by hydrogen, halogen cyano, sulfo, alkali or ammonium salts of sulfo, carboxy, substituted or unsubstituted alkyl, perfluoroalkyl, alkoxy, alkylthio, nitro, amino, monoalkylamino, dialkylamino, substituted or unsubstituted aryl substituents, substituted or unsubstituted heteroaryl substituents, or additional substituted or unsubstituted fused benzo rings or substituted or unsubstituted fused heteroaromatic rings. Any alkyl substituent present on the subject dye is optionally further substituted by a reactive site, or a functional group that can be readily converted into a reactive site.

30 Claims, 4 Drawing Sheets

DIBENZOPYRROMETHENEBORON DIFLUORIDE DYES

FIELD OF THE INVENTION

The present invention relates to fluorescent compounds, in particular fluorescent dyes having a core structure that is a 3,4:3',4'-dibenzopyrrometheneboron difluoride. The dyes of the present invention are useful as detection reagents, and are optionally incorporated in a variety of materials.

BACKGROUND OF THE INVENTION

Dyes in general, and fluorescent dyes in particular, are often used to directly stain or label a sample so that the sample can be identified or quantitated. For instance, such dyes may be added as part of an assay for a biological target analyte, as a detectable tracer element in a biological or non-biological fluid, or for such purposes as photodynamic therapy of tumors, in which a dyed sample is irradiated to selectively destroy tumor cells and tissues, or to photoablate arterial plaque or cells. Furthermore, fluorescent dyes can often be chemically modified so that they can be covalently attached to a variety of materials to give them desirable fluorescent characteristics.

Fluorescent dyes with longer wavelength absorption and emission are particularly useful in conjunction with materials of biological origin such as blood, urine, fecal matter, cells and tissues, where background or inherent fluorescence or absorption often interferes with detection of the added fluorescent dye. Furthermore, biological specimens often have decreasing levels of both absorption and fluorescence emission as the illumination energy approaches the infrared. In addition, numerous biological and nonbiological applications of long wavelength dyes exist, including use as laser dyes, or in electronics as optical memory elements using relatively low cost illumination sources such as laser diodes. Consequently, dyes that possess these spectral properties have potential utility in biological and non-biological applications.

A variety of dipyrrometheneboron difluoride dyes (4,4-difluoro-4-bora-3a,4a-diaza-s-indacenes) have previously been described, by these inventors, and others, in which substituents are attached by a single covalent bond, including U.S. Pat. Nos. 4,774,339 to Haugland et al. and U.S. Pat. No. 5,274,113 to Kang et al. (reactive substituents), U.S. Pat. No. 5,248,782 to Haugland et al. (heteroaryl substituents), U.S. Pat. No. 5,178,288 to Kang et al. (ethenyl substituents), and Ser. No. 07/654,881 by Kang et al., filed 2/13/91 (fatty acid substituents). All the above issued and pending patents describe fluorescent dyes and conjugates of fluorescent dyes based on the dipyrrometheneboron difluoride core structure shown below:

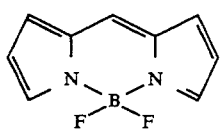

The use of derivatives of dipyrrometheneboron difluoride (particularly symmetrical alkyl derivatives and alkyl derivatives that are also sulfonated) as laser dyes is described in U.S. Pat. No. 4,916,711 to Boyer, et al.

None of the above references described dipyrrometheneboron difluoride dyes that incorporate fused aromatic rings, as found in the compounds of the present invention that are based on the 3,4:3',4'-dibenzopyrrometheneboron difluoride core structure below:

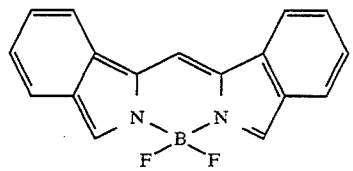

The synthetic route to the dibenzopyrrometheneboron difluoride dyes (described in detail below) proceeds through the condensation of 2-acylacetophenones. This synthetic route is very different from that used for previously described dipyrrometheneboron difluoride fluorophores. Furthermore, the dyes of the present invention cannot be prepared using the previous method, due to the instability of the isoindole nucleus.

Aryl-substituted derivatives of the key intermediate in the synthesis of some of the instant dyes, dibenzopyrromethenes, are isolable compounds that were originally described by Maekawa et al. (CHEM. BER. 101, 847 (1968)). This reference does not teach or recommend the conversion of the dibenzopyrromethene intermediate to the subject dyes, and does not indicate that such dyes would possess any of the desirable properties possessed by the dyes of the present invention.

The dyes of the present invention typically possess longer wavelength excitation and emission bands than previously described dipyrrometheneboron difluoride dyes. In addition, the spectral properties of the dyes are substantially insensitive to the chemical environment of the dye, even when compared to the previously described dipyrrometheneboron difluoride dyes. Practically this means that the absorbance and emission of the dyes differ only slightly when measured in different solvents. The subject dyes are stable to photobleaching, remaining intensely fluorescent even when constantly illuminated. Finally, selected dyes of the present invention possess exceptionally narrow excitation bands coupled with very high extinction coefficients. The combination of these favorable properties make dibenzopyrrometheneboron difluoride dyes exceptionally useful fluorophores for a variety of applications.

DESCRIPTION OF THE DRAWINGS

FIG. 4: A comparison of the photostability of a solution of Compound 3 versus a solution of fluorescein. Each solution was prepared with an optical density of

SUMMARY OF THE INVENTION AND DESCRIPTION OF PREFERRED EMBODIMENTS

Figure 1:
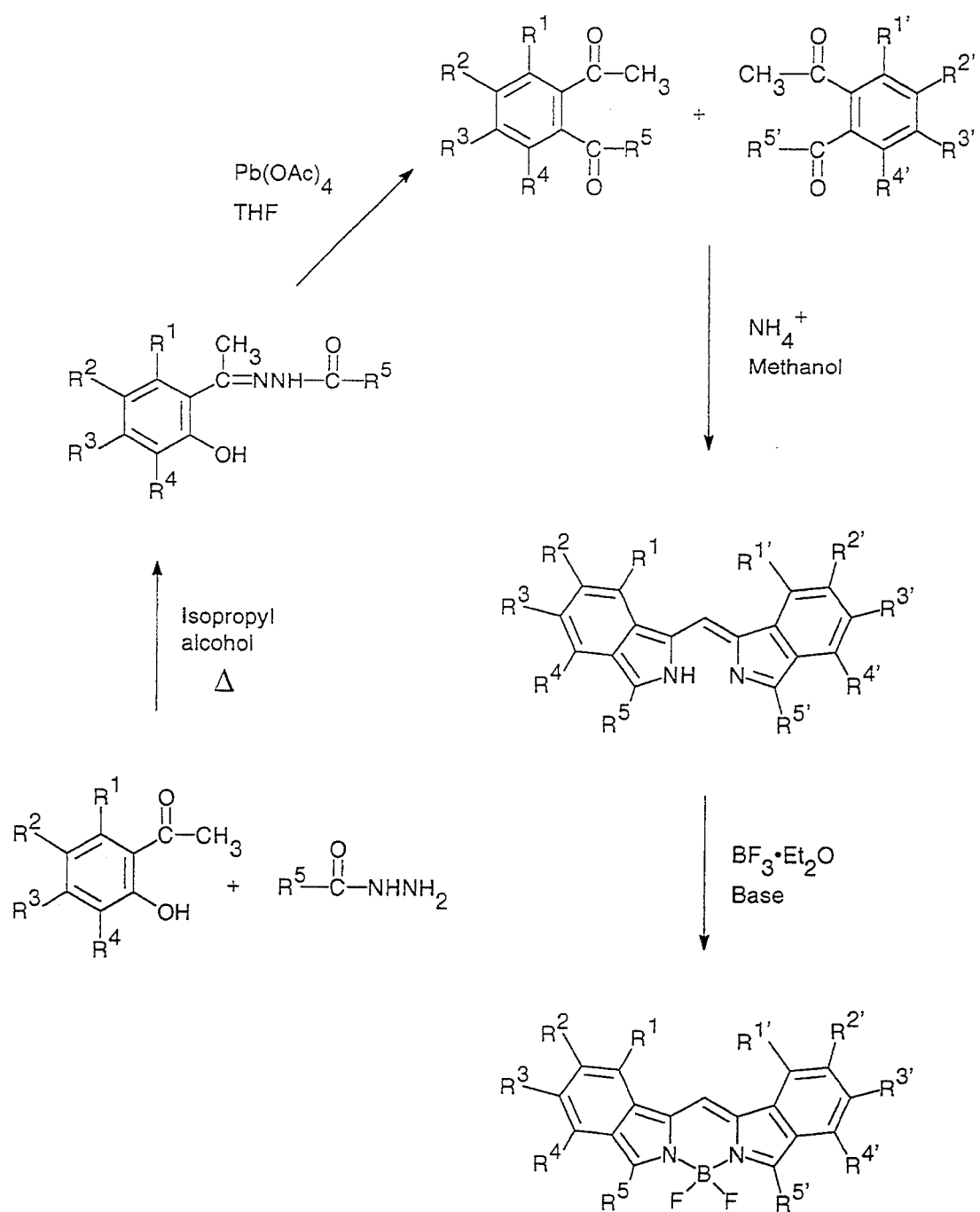
FIG. 1: A generalized synthetic scheme for the preparation of the substituted dibenzopyrrometheneboron difluoride dyes of the present invention.
Figure 2:
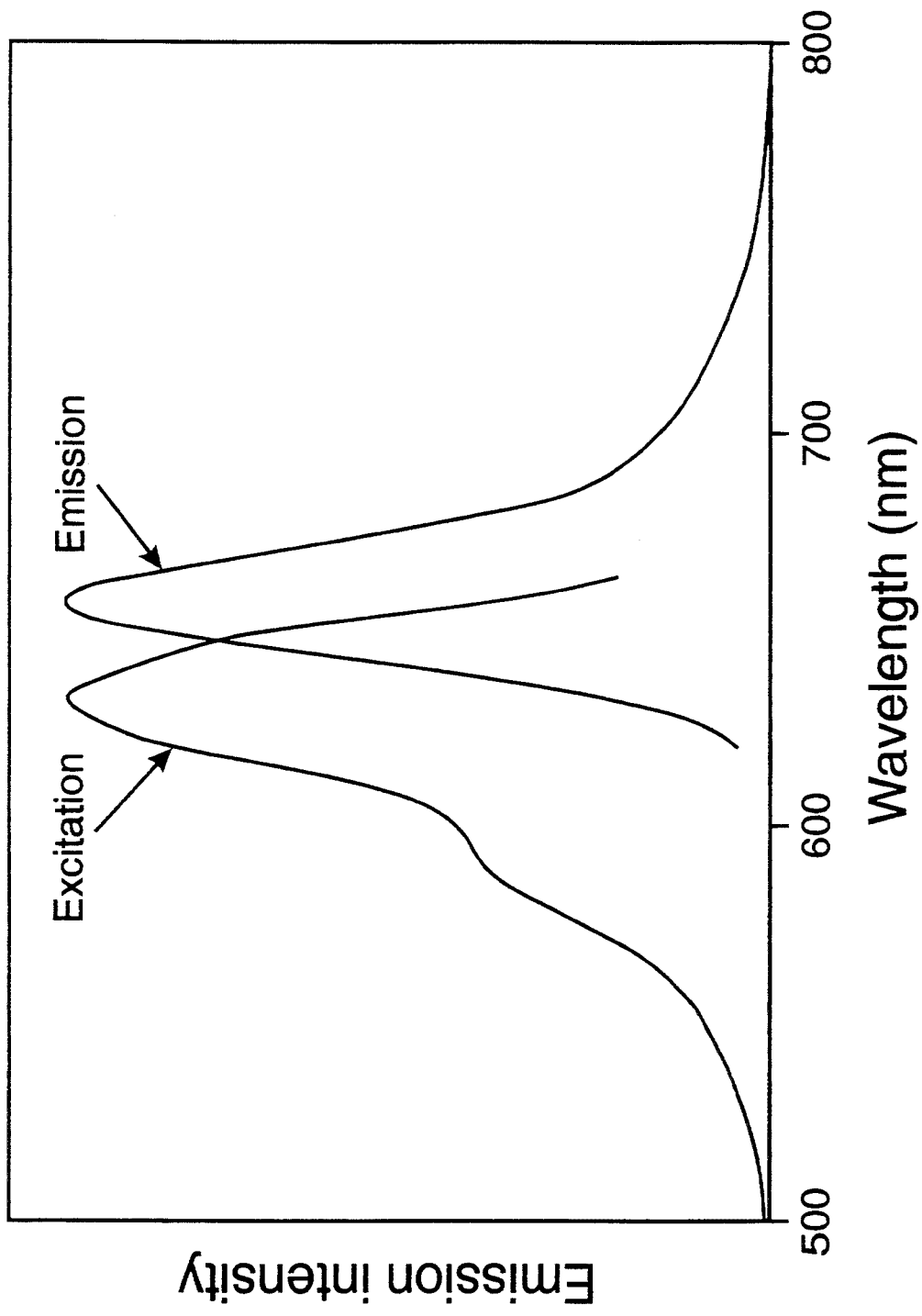
FIG. 2: The excitation and emission spectra of a methanol solution of Compound 3, measured using a Perkin-Elmer Model 650-40 fluorometer with illumination at 633 nm.
Figure 3:
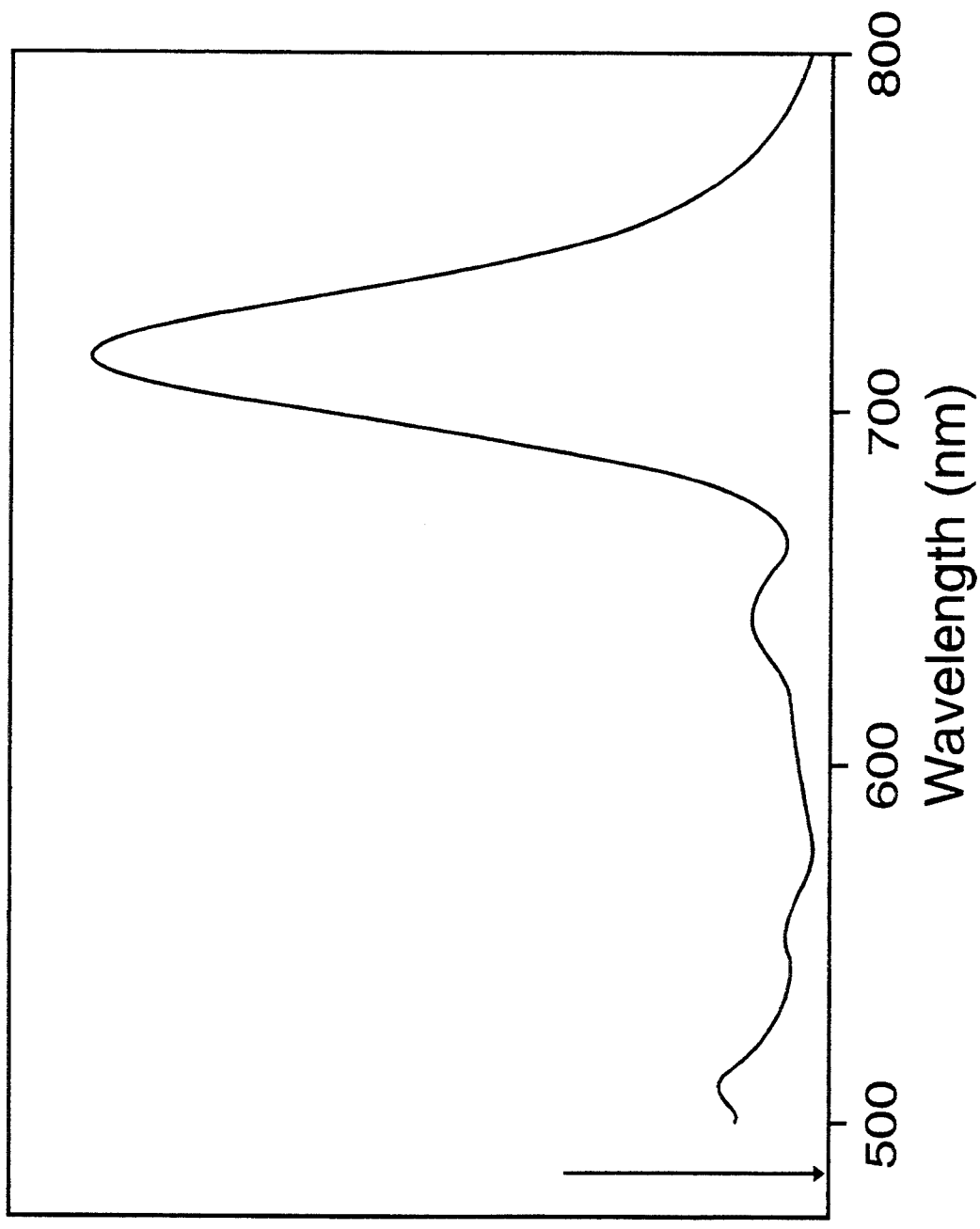
FIG. 3: The emission spectrum of a 1 μm latex particle containing multiple fluorescent dyes, one of which is Compound 5. The arrow indicates the 488 nm spectral line of an argon laser, used to excite the initial fluorescent dye. Energy transfer between successive fluorescent dyes present in the particle results in maximum fluorescent emission by Compound 5 at about 715 nm.

The compounds of the present invention are substituted or unsubstituted derivatives of 1-[isoindolyl]-methylene-isoindole that are bound through both isoindole nitrogens to a boron difluoride moiety, forming a fluorescent dibenzopyrrometheneboron difluoride compound whose fluorescence properties are modified by the selection of appropriate chemical substituents.

The benzo rings of the dibenzopyrrometheneboron difluoride core structure of the dyes of the present invention is optionally substituted by substituents that are be used to modify the spectral properties, solubility or other physical properties of the dye. The dyes are also optionally substituted by additional fused benzo rings or fused heteroaromatic rings. Any substituent present on the subject dye is optionally further substituted by a reactive site, or a functional group that can be readily converted into a reactive site. Alternatively, the subject dye is covalently attached to a natural or synthetic conjugant.

The substituents on the subject dye are selected from hydrogen, halogen, cyano, sulfo, carboxy, alkyl, perfluoroalkyl, cycloalkyl, alkoxy, alkylthio, substituted or unsubstituted aryl substituents, and substituted or unsubstituted heteroaryl substituents. All substituents have less than or equal to 25 carbon atoms.

Specific embodiments of the dyes of the present invention are described by the formula:

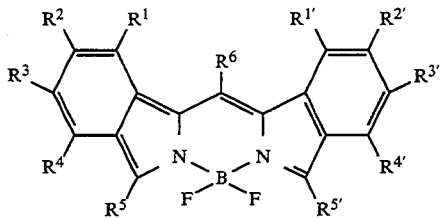

The ring substituents $R^1$, $R^2$, $R^3$, $R^4$, $R^{1'}$, $R^{2'}$, $R^{3'}$, and $R^{4'}$ are independently H, halogen (including F, Cl, Br or I), cyano, sulfo, alkali or ammonium salts of sulfo, carboxy, alkyl, perfluoroalkyl, alkoxy, alkylthio, nitro, amino, monoalkylamino, dialkylamino, alkylamido; or substituted or unsubstituted ARYL, ARYL-oxy, HETEROARYL, HETEROARYL-oxy, ARYL-amino, HETEROARYL-amino, ARYL-amido, or HETEROARYL-amido; or two adjacent positions are fused to additional BENZO or HETERO rings.

As used herein, amido is a linking moiety that has the formula —NH(C=O)— or —(C'O)—NH—. That is, alkylamido, ARYL-amido and HETEROARYL-amido can be attached to the dye through the carbonyl carbon or through the amide nitrogen atom.

All alkyl portions of alkyl, alkoxy, perfluoroalkyl, alkylthio, monoalkylamino, dialkylamino or alkylamido substituents contain 1–18 carbon atoms in an arrangement that is either linear or branched. The alkyl portions of such substituents are optionally further substituted by any synthetically accessible and chemically stable combination of substituents that are independently H, halogen, cyano, amino, amido, hydroxy, carboxy, mercapto, sulfo, or alkali or ammonium salt of sulfo.

Where a ring is substituted by BENZO, any two adjacent positions of $R^1$, $R^2$, $R^3$, $R^4$, $R^{1'}$, $R^{2'}$, $R^{3'}$, and $R^{4'}$ are bonded by —$CR^7$=$CR^8$—$CR^9$=$CR^{10}$— to form a benzo-fused derivative in which the substituents $R^7$, $R^8$, $R^9$ and $R^{10}$ are independently selected from the same set of substituents as permitted for $R^1$, $R^2$, $R^3$, $R^4$, $R^{1'}$, $R^{2'}$, $R^{3'}$, and $R^{4'}$. The dyes of the present invention are optionally substituted by up to four BENZO substituents, with no more than two additional BENZO groups present on a single aromatic ring.

Where a ring is substituted by HETERO, any two adjacent positions of $R^1$, $R^2$, $R^3$, $R^4$, $R^{1'}$, $R^{2'}$, $R^{3'}$, and $R^{4'}$ are bonded by a combination of 1 to 3 carbon atoms and 1 to 3 hetero atoms selected from the group consisting of O, S and N to form a fused 5- or 6-membered heteroaromatic ring. The remaining positions on the fused heteroaromatic ring are optionally and independently substituted by any synthetically accessible and chemically stable combination of substituents that are independently H, halogen, cyano, sulfo, alkali or ammonium salt of sulfo, carboxy, alkyl, perfluoroalkyl, alkoxy, alkylthio, amino, monoalkylamino, dialkylamino or alkylamido.

Where a ring substituent is ARYL, ARYL is defined as an aromatic or polyaromatic substituent containing 1 to 4 aromatic rings (each ring containing 6 conjugated carbon atoms and no heteroatoms) that are optionally fused to each other or bonded to each other by carbon-carbon single bonds. ARYL is bound to the dye by a single bond and is optionally substituted as described below.

Specific examples of the ARYL moiety include, but are not limited to, substituted or unsubstituted derivatives of phenyl, biphenyl, o-, m-, or p-terphenyl, 1-naphthyl, 2-naphthyl, 1-, 2-, or 9-anthryl, 1-, 2-, 3-, 4-, or 9-phenanthrenyl and 1-, 2- or 4-pyrenyl. Preferably ARYL is phenyl, substituted phenyl, naphthyl or substituted naphthyl. The choice of ARYL moieties is dependent on the properties desired for the resulting dye. When ARYL is phenyl, the synthetic preparation of the dye is simplified. However, when ARYL is naphthyl the fluorescence emission of the resulting dye is shifted to shorter wavelengths and typically has a higher quantum yield.

Where a ring substituent is HETEROARYL, HETEROARYL is defined as a 5- or 6-membered heteroaromatic ring that is optionally fused to an additional six-membered aromatic ring(s), or is fused to one 5- or 6-membered heteroaromatic ring. The heteroaromatic rings contain at least 1 and as many as 3 heteroatoms that are selected from the group consisting of O, N or S in any combination. HETEROARYL is attached to the dye by a single bond, and is optionally substituted as defined below.

Specific examples of the HETEROARYL moiety include, but are not limited to, substituted or unsubstituted derivatives of 2- or 3-furanyl; 2- or 3-thienyl; N-, 2- or 3-pyrrolyl; 2- or 3-benzofuranyl; 2- or 3-benzothienyl; N-, 2- or 3-indolyl; 2-, 3- or 4-pyridyl; 2-, 3- or 4-quinolyl; 1-, 3-, or 4-isoquinolyl; 2-, 4-, or 5-(1,3-oxazolyl); 2-benzoxazolyl; 2-, 4-, or 5-(1,3-thiazolyl); 2-benzothiazolyl; 3-, 4-, 5-isoxazolyl; N-, 2-, or 4-imidazolyl; N-, or 2-benzimidazolyl; 1- or 2-naphthofuranyl; 1- or 2-naphthothienyl; N-, 2- or 3-benzindolyl; 2-, 3-, or 4-benzoquinolyl; 1-, 2-, 3-, or 4-acridinyl. Preferably HETEROARYL is substituted or unsubstituted 4-pyridyl, 2-thienyl, 2-pyrrolyl, 2-oxazolyl, 2-benzothiazolyl or 2-benzoxazolyl. More preferably, HETEROARYL is 2-thienyl or 2-pyrrolyl.

The ARYL or HETEROARYL moieties are unsubstituted or optionally and independently substituted by any synthetically accessible and chemically stable combination of substituents that are independently H, halogen, cyano, sulfo, alkali or ammonium salt of sulfo, nitro, carboxy, alkyl, perfluoroalkyl, alkoxy, alkylthio, amino, monoalkylamino, dialkylamino or alkylamido.

The substituents $R^5$ and $R^{5'}$ are independently selected from the group consisting of substituted or unsubstituted alkyl, cycloalkyl having 3–6 carbons, perfluoroalkyl, ARYL or HETEROARYL. Preferably $R^5$ and $R^{5'}$ are ARYL or HETEROARYL. Dibenzopyrromethenboron difluoride dyes substituted only by alkyl or cycloalkyl substituents at $R^5$ or $R^{5'}$ are somewhat unstable, and are not preferred.

The substituent $R^6$ is one of H, alkyl, cycloalkyl having 3–6 carbons, perfluoroalkyl, ARYL or HETEROARYL. Preferably, $R^6$ is H or ARYL.

Table 1 shows the chemical structures of selected embodiments of the dyes of the present invention.

TABLE 1
Selected Dyes of the Present Invention

Compound 2

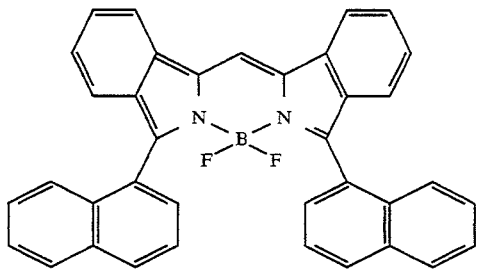

Compound 3

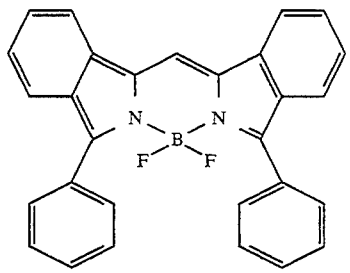

Compound 5

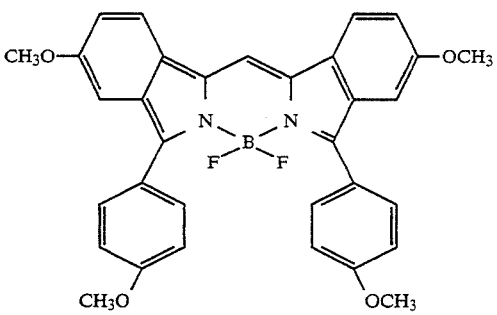

Compound 7

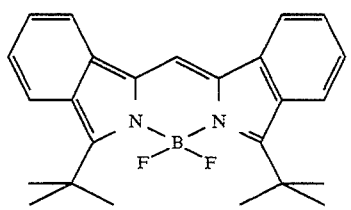

Compound 8

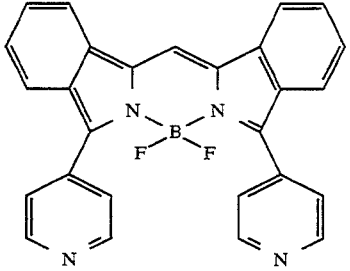

Compound 10

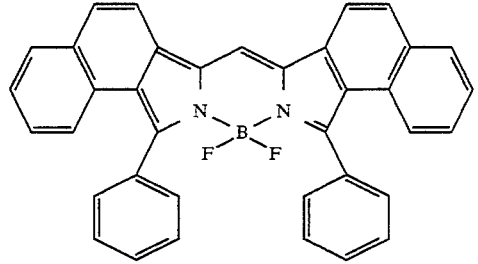

Compound 11

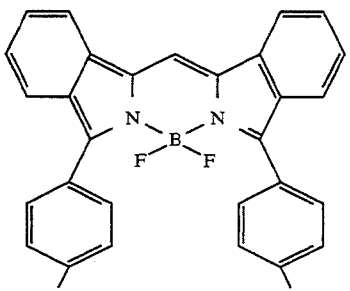

Compound 12

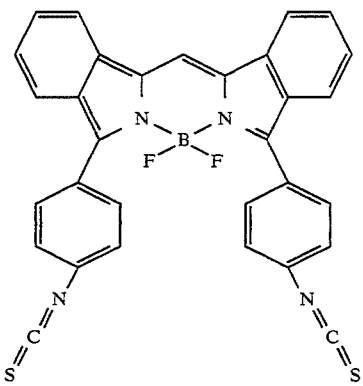

TABLE 1-continued
Selected Dyes of the Present Invention
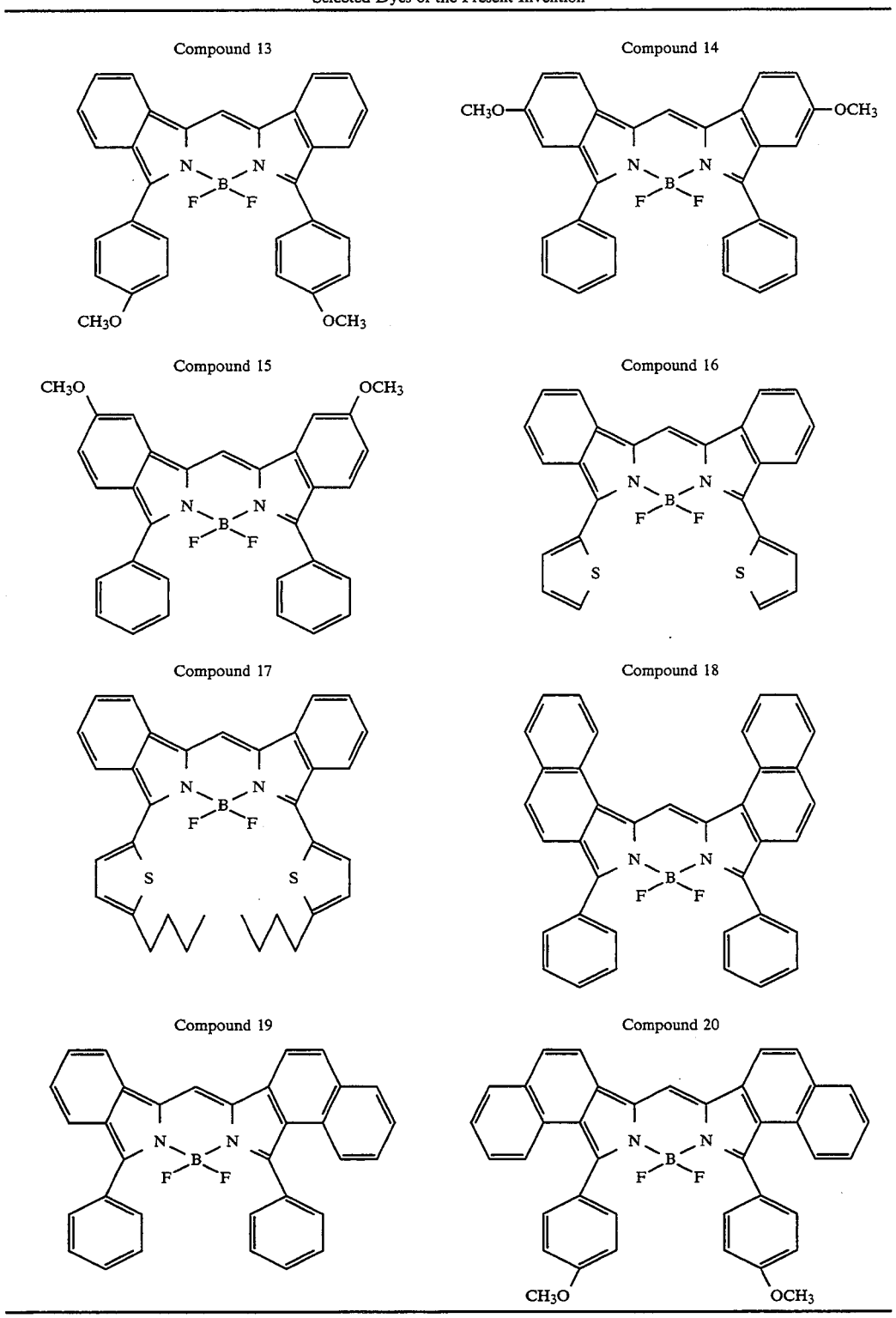
A particularly suitable synthesis for symmetrically-substituted dibenzopyrromethene boron difluoride dyes (FIG. 1) requires initial preparation of a suitably substituted 2-acylacetophenone precursor or one of its fused analogs:

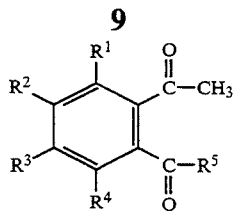

Numerous 2-acylacetophenones undergo condensation in the presence of ammonia or ammonium salts to give the dibenzopyrromethene intermediate necessary to prepare the subject dyes (Maekawa et al. supra). While a number of reactions have been reported for the preparation of 2-acylacetophenone or structurally related precursors (e.g. Weygand et al. CHEM. BER. 89, 1994 (1956), Dierichs et al. CHEM. BER. 90, 1208 (1957) and Newman J. ORG. CHEM. 26, 2630 (1961)), the general method reported by Kotali et al. (TET. LETT. 28, 4321 (1987)) is particularly useful for the preparation of these key precursors (see FIG. 1).

Typically, the 2-acylacetophenone precursor is selected so as to yield the desired dibenzopyrromethene boron difluoride dye. The precursors must therefore be appropriately substituted or possess substituents that are suitably protected and can be deprotected after the dibenzopyrrometheneboron difluoride dye is prepared.

Substituents at the $R^5$ position can be easily incorporated into the 2-acylacetophenone precursor. The requisite hydrazide ($R^5$—(C'O)—$NHNH_2$) is commercially available, or can be readily prepared from the corresponding acid, ester or other derivatives and hydrazine by reactions familiar to anyone skilled in the art (see Example 8). Condensation of $R^5$—(C=O)—$NHNH_2$ with the carbonyl moiety of the acetyl group is usually facile (see Examples 1, 5, 8 and 12 and FIG. 1). Appropriately-substituted or fused variations of the 2-hydroxyacetophenone precursor are readily prepared by a Fries rearrangement of the phenolic acetates (ORG. SYNTH. coll. vol. 2, 543).

The condensation of 2-acylacetophenones is only useful for producing intermediates for which the substituent $R^6$ is hydrogen. If a non-hydrogen $R^6$ substituent is desired, an alternate synthesis is required. As described in the Chemical Abstracts 79:126122r (1973) and 82:72716d (1975) (Svirevski et al. and Minchev et al., respectively) dibenzopyrromethene intermediates where $R^6$ is phenyl can be prepared by heating an appropriately substituted hydrindenone with aqueous ammonia in a sealed tube. This synthetic route can be modified by methods known in the art to yield other desired $R^6$ substituents.

Upon synthesizing an appropriately substituted (or protected) dibenzopyrromethene intermediate, the formation of the dibenzopyrrometheneboron difluoride dye is accomplished by reaction of the intermediate with boron trifluoride in combination with an organic or inorganic base. Boron trifluoride is preferably used as an ether complex, due to the difficulty of handling the gaseous reagent (see Examples 3, 4, 7, 11 and 14). Suitable bases include, but are not limited to, trimethylamine, triethylamine, N,N-diisopropylethylamine, N,N,N',N'-tetramethylethylenediamine, 1,8-bis(dimethylamino)naphthalene, diazabicyclooctane, diazabicycloundecene, 4-dimethylaminopyridine, 4-pyrrolidinopyridine and other similar bases. Most of the resulting dibenzopyrrometheneboron difluoride dyes are chemically stable, highly colored compounds that can be readily purified by crystallization or preparative chromatography.

Symmetric dibenzopyrrometheneboron difluoride dyes (where $R^1=R^{1'}$, $R^2=R^{2'}$, $R^3=R^{3'}$, $R^4=R^{4'}$ and $R^5=R^{5'}$) are readily prepared from the use of a single, appropriately-substituted 2-acylacetophenone precursor. After condensation, the resulting dibenzopyrromethene intermediate is symmetrical, and treatment with boron trifluoride yields a symmetrical fluorescent dye.

Asymmetric dibenzopyrrometheneboron difluoride dyes are the dyes of the present invention for which at least one of the substituents at $R^1$, $R^2$, $R^3$, $R^4$ or $R^5$ differs from the corresponding substituent at $R^{1'}$, $R^{2'}$, $R^{3'}$, $R^{4'}$ or $R^{5'}$. Asymmetric dyes are prepared analogously to the symmetric dyes, excepting that two different 2-acylacetophenone precursors, in approximately equivalent proportions, are condensed to give an asymmetric dibenzopyrromethene intermediate. This condensation process necessarily yields three products in an approximately statistical distribution—two symmetric dibenzopyrromethene intermediates, and one (desired) asymmetric intermediate. It is usually necessary to chromatographically separate the asymmetric dye from the two different symmetric dyes. The difficulty in preparing pure asymmetric dyes is typically greater, and the yield is typically much lower, than that of the symmetrical dyes. However, this synthetic route can be required, if a dibenzopyrrometheneboron difluoride dye having a single reactive site or ligant as a substituent is desired.

The described method for synthesis of the key intermediates permits incorporation of a wide variety of substituents at any position of the ultimate dibenzopyrrometheneboron difluoride dye, except at the bridgehead position in the boradiazine ring. Bridgehead substituents can be incorporated using alternative syntheses (Svirevski et al. and Minchev et al., supra). The allowed substituents include functional groups that are chemically reactive (or than can be made chemically reactive) with the functional groups typically found in biological materials or polymers, or functional groups that can be readily converted to chemically reactive derivatives using methods well known in the art (Haugland, MOLECULAR PROBES HANDBOOK OF FLUORESCENT PROBES AND RESEARCH CHEMICALS, Sets 1–11, (1992)). Some examples of this type of conversion include:

1. The activation of amine groups to yield reactive species, including isocyanates, isothiocyanates, 4,6-dichloro-1,3,5-triazines, maleimides or haloacetamides;
2. The conversion of carboxylic acid groups to activated derivatives, including symmetric and mixed anhydrides, acid halides, acyl azides, acyl hydrazides and various activated esters, including succinimidyl esters, p-nitrophenyl esters and pentafluorophenyl esters;
3. The conversion of sulfo groups to sulfonyl chlorides and sulfonyl fluorides;
4. The conversion of alcohols groups to ethers, esters, urethanes, carbonates or alkylating agents that include sulfonate esters and halides;
5. The conversion of thiols to thioethers, thioesters and disulfides;

PHYSICAL AND SPECTRAL PROPERTIES

The fluorescent dyes of the present invention possess several attractive features that make them useful in a variety of applications. The absorption transition of the instant dyes is quite intense, with molar absorptivities generally exceeding 80,000 cm$^{-1}$M$^{-1}$, typically exceeding 100,000 cm$^{-1}$M$^{-1}$ and occasionally exceeding 240,000 cm$^{-1}$M$^{-1}$. The quantum yields of fluorescence emission in organic solvents are typically greater than 0.3, frequently greater than 0.7 sometimes greater than 0.9. In addition, the dyes of the present invention are typically stable to photobleaching. Certain embodiments of the present invention have exhibited greater photostability than does fluorescein (see FIG. 5).

The subject dyes and their derivatives typically have an absorption maximum that is greater than 600 nm, and an emission maximum that is greater than 650 nm. As described above, the core structure of the instant dyes can be modified by substitution of chemical moieties, including aryl or heteroaryl groups, or by fusion of the structure to additional aromatic or heteroaromatic rings. With proper selection of chemical substituents, the excitation and emission wavelengths of the subject dyes are extended beyond 700 nm, typically without the loss of other desirable photophysical properties.

Table 2 lists the absorption and emission properties of selected examples of dibenzopyrrometheneboron difluoride dyes, including some that incorporate fused rings. Overall it is observed that fusion of the benzo moiety to the indacene rings of the previously-described 4,4-difluoro-4-bora-3a,4a-diaza-s-indacene dyes (dipyrrometheneboron difluoride) bathochromically shifts the absorption spectrum and emission by about 80 nm from the similarly substituted dibenzopyrrometheneboron difluoride dyes. For example, compare Compound 3 in Table 2, having an absorption maximum of 634 nm and emission maximum of 658 nm in methanol, with the similarly substituted 4,4-difluoro-3,5-diphenyl-4-bora-3a,4a-diaza-s-indacene, which has maximal absorbance at 550 nm and emission at 580 nm in methanol.

Unexpectedly, the fusion of additional benzo rings on the dibenzopyrrometheneboron difluoride core structure (as for Compound 10, Table 2) results in a shift of both excitation and emission bands to shorter wavelengths relative to dyes of the present invention hat do not possess additional fused rings. The dyes of the invention that possess extended ring systems of this type also possess exceptionally narrow emission bands and very high extinction coefficients.

While most fluorescent dyes exhibit a substantial solvent effect, it is observed that the spectral properties of the subject dyes are unusually insensitive to the effect of different solvents. Absorption maxima for Compound 3 measured in several organic solvents show a range of only 12 nm (Table 3), while the emission maxima measured in the same solvents show a range of 10 nm. Some fluorescent dyes can display a shift in emission of excitation of as much as 100 or more nm when the solvent system is changed.

As has previously been observed, the substitution of aryl, heteroaryl, alkenyl, polyalkenyl, alkynyl or polyalkynyl groups onto the structurally similar dibenzopyrrometheneboron difluoride dyes can dramatically shift the wavelength of maximum absorption and emission to longer wavelengths (U.S. Pat. No. 5,248,782 to Haugland et al., supra). Even the position of substitution on the benzo moiety by the same substituent, such as methoxy, can effect the spectral properties in a controllable fashion (for example, Compounds 5, 13 and 14 in Table 2). With appropriate design and careful synthesis, a family of dibenzopyrrometheneboron difluoride dyes with varied and distinct spectral properties can be prepared.

TABLE 2

Spectral Properties of Selected Symmetrical Dibenzopyrrometheneboron Difluoride Dyes

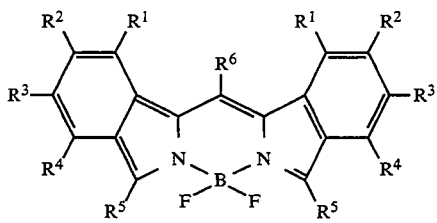

| Compound | Substituents | $\lambda_{Abs}$ max (nm) † | $\epsilon \times 10^{-3}$ (cm$^{-1}$M$^{-1}$)† | $\lambda_{Em}$ max (nm) † | Quantum Yield ($\varnothing$) ‡ |
|---|---|---|---|---|---|
| 2 | $R^1$-$R^4$ = H, $R^5$ = 1-naphthyl, $R^6$ = H | 621 | 118.7 | 645 | 1.00 |
| 3 | $R^1$-$R^4$ = H, $R^5$ = phenyl, $R^6$ = H | 634 | 108.4 | 658 | 0.92 |
| 5 | $R^1$ = $R^2$ = $R^4$ = H, $R^3$ = methoxy, $R^5$ = 4-methoxyphenyl, $R^6$ = H | 673 | 118.6 | 704 | 0.51 |
| 7 | $R^1$-$R^4$ = H, $R^5$ = t-butyl, $R^6$ = H | 571 | ND | 597 | ND |
| 8 | $R^1$-$R^4$ = H, $R^5$ = 4-pyridyl, $R^6$ = H | 644 | 95.6 | 671 | 0.78 |
| 10 | $R^1$ = $R^2$ = H, $R^3$ = $R^4$ = —CH=CH—CH=CH—, $R^5$ = phenyl, $R^6$ = H | 605 | 249.3 | 616 | 1.00 |
| 11 | $R^1$-$R^4$ = H, $R^5$ = 4-nitrophenyl, $R^6$ = H | 659 | ND | 698 | ND |

TABLE 2-continued

Spectral Properties of Selected Symmetrical Dibenzopyrrometheneboron Difluoride Dyes

| Compound | Substituents | $\lambda_{Abs}$ max (nm) † | $\epsilon \times 10^{-3}$ (cm$^{-1}$M$^{-1}$) † | $\lambda_{Em}$ max (nm) † | Quantum Yield (∅) ‡ |
|---|---|---|---|---|---|
| 13 | $R^1$-$R^4$ = H, $R^5$ = 4-methoxyphenyl, $R^6$ = H | 646 | 104.8 | 673 | 0.71 |
| 14 | $R^1$ = $R^2$ = $R^4$ = H, $R^3$ = methoxy, $R^5$ = phenyl, $R^6$ = H | 663 | 95.7 | 690 | 0.57 |
| 15 | $R^1$ = $R^3$ = $R^4$ = H, $R^2$ = methoxy, $R^5$ = phenyl, $R^6$ = H | 625 | ND | 652 | ND |
| 16 | $R^1$-$R^4$ = H, $R^5$ = 2-thienyl, $R^6$ = H | 680 | ND | 713 | 0.35 |
| 17 | $R^1$-$R^4$ = H $R^5$ = 2-(5-butyl)thienyl, $R^6$ = H | 696 | 81.6 | 732 | 0.19 |
| 18 | $R^1$-$R^2$ = —CH=CH—CH=CH—, $R^3$ = $R^4$ = H, $R^5$ = phenyl, $R^6$ = H | 653 | ND | 670 | 0.34 |
| 20 | $R^1$ = $R^2$ = H, $R^3$ = $R^4$ = —CH=CH—CH=CH—, $R^5$ = 4-methoxyphenyl, $R^6$ = H | 609 | 184.0 | 630 | .86 |

† Absorption maxima ($\lambda_{Abs}$ max) and emission maxima ($\lambda_{Em}$ max) were measured in methanol solution except Compound 15 (in chloroform) and Compound 7 (in dichloromethane). Extinction coefficients ($\epsilon$) are shown in units of $10^3 \times$ cm$^{-1}$M$^{-1}$ at their absorption maxima in methanol solution.
‡ Fluorescence quantum yields ( ) in methanol were measured relative to Nile Blue ( = 0.25) for Compounds 2–8 and 13–20 and Cresyl Violet ( = 0.54) for Compound 10.
ND = not determined.

TABLE 3

Spectral Properties of Compound 3 in Selected Solvents

| Solvent | $\lambda_{Abs}$ max (nm) | $\epsilon \times 10^{-3}$ (cm$^{-1}$M$^{-1}$) † | $\lambda_{Em}$ max (nm) | Quantum Yield (∅) ‡ |
|---|---|---|---|---|
| methanol | 634 | 108.4 | 658 | 0.92 |
| chloroform | 644 | 102.5 | 667 | 0.73 |
| acetonitrile | 633 | 106.8 | 657 | 1.00 |
| dioxane | 639 | 112.7 | 660 | 0.84 |
| toluene | 645 | 108.5 | 663 | 0.61 |
| hexane | 638 | 115.8 | 657 | 0.89 |

† Extinction coefficients ($\epsilon$) are shown in units of $10^3 \times$ cm$^{-1}$M$^{-1}$ at their absorption maxima.
‡ Fluorescent quantum yield ( ) were measured relative to Nile Blue ( = 0.25).

APPLICATIONS

The long-wavelength excitation and emission bands of dibenzopyrrometheneboron difluoride dyes, coupled with their high absorbance and quantum yields, give the subject dyes utility in a variety of applications.

In one aspect of the invention, dibenzopyrrometheneboron difluoride dyes possess utility as laser dyes according to methods known in the art (e.g. Boyer et al., supra, incorporated by reference). As discussed above, the long wavelength excitation bands of the subject dyes allow the use of inexpensive laser diodes as excitation sources for dye lasers utilizing the subject dyes.

In another aspect of the invention, the dyes of the present invention can be used to stain samples and sample solutions. Typically the dyes of the present invention are highly colored, and can be detected visually or colorimetrically. Alternatively, the dye is detected using its fluorescence properties. To observe fluorescence, the sample is first excited by a light source capable of producing light at or near the wavelength of maximum absorption of the dye, such as a visible lamp, a laser, or even sunlight. Preferably the dye is excited at a wavelength equal to or greater than about 600 nm, more preferably equal to or greater than about 650 nm. The fluorescence of the dye is detected qualitatively or quantitatively by detection of the resultant light emission at a wavelength of greater than about 650 nm, preferably greater than about 700 nm. The emission is detected by means that include visible inspection, photographic film, or the use of current instrumentation such as fluorometers, quantum counters, plate readers, epifluorescence microscopes and flow cytometers, or by any means for amplifying the signal, such as a photomultiplier or cooled charge-coupled device (CCD).

In another aspect of the invention, dyes of the present invention are covalently attached to a desired conjugant. As used herein, a conjugant is any molecule, substance or material that can be covalently attached to the dye to yield a dye-conjugate. Preferably, because of the relative ease of synthesis, dyes that are substituted by amines, alcohols, thiols or acids are generally utilized to prepare the labeled conjugates. Selected conjugants include, but are not limited to, antibodies, amino acids, proteins, peptides, polypeptides, enzymes, enzyme substrates, hormones, lymphokines, metabolites, antigens, haptens, lectins, avidin, streptavidin, toxins, poisons, environmental pollutants, carbohydrates, oligosaccharides, polysaccharides, glycoproteins, glycolipids, nucleotides, oligonucleotides, nucleic acids and derivatized nucleic acids (including deoxyribo- and ribonucleic acids), DNA, and RNA fragments and derivatized fragments (including single and multi-stranded fragments), natural and synthetic drugs, receptors, virus particles, bacterial particles, virus components, biological cells, cellular components (including cellular membranes and organelles), natural and synthetic lipid vesicles, polymers, polymer particles, polymer membranes, and glass and plastic surfaces and particles.

Methods of preparing conjugates of this type using a reactive fluorophore are well known in the art (Haugland, MOLECULAR PROBES HANDBOOK, supra). The resulting conjugates are easily detectable by virtue of the fluorescence of the bound fluorophore, as discussed above. Such labeled conjugates make possible a variety of assays for biomolecules and biological components, including fluorescent immunoassays, receptor labeling and fluorescence hybridization assays.

In an additional embodiment of the invention, the dyes of the present invention are used to label polymer microparticles. As used herein the polymer microparticle can be prepared from a variety of polymers including, but not limited to nitrocellulose, polystyrene (including high density polystyrene latexes such as brominated polystyrene), polymethylmethacrylate and other polyacrylic acids, polyacrylonitrile, polyacrylamide, polyacrolein, polydimethylsiloxane, polybutadiene, polyisoprene, polyurethane, polyvinylacetate, polyvinylchloride, polyvinylpyridine, polyvinylbenzylchloride, polyvinyltoluene, polyvinylidene chloride, and polydivinylbenzene. Preferably, the polymer microparticle is prepared from polystyrene or polyacrylamide. Preferred polymers are polystyrene-based, optionally copolymerized with a cross-linking agent such as divinylbenzene. Suitable particles that are also magnetic are available from Dynal (Lake Success, N.Y.) and other sources.

The microparticles can be manufactured in a variety of useful sizes and shapes. They may be spherical or irregular in shape, and range in size from about 0.01 micrometers to about 50 micrometers. Typically, the labeled microparticles are less than about 15 micrometers in diameter and are spherical. More typically the microparticle is a microsphere less than about 5 micrometers in diameter. The microparticles may be of uniform size and/or shape or non-uniform.

One or more species of dibenzopyrromethenboron difluoride dyes can be associated with polymeric microparticles, either covalently or non-covalently, essentially as described in co-pending applications DIPYRROMETHENEBORON DIFLUORIDE LABELED FLUORESCENT MICROPARTICLES by Brinkley et al., Ser. No. 07/629,466, filed 12/18/90; FLUORESCENT MICROPARTICLES WITH CONTROLLABLE ENHANCED STOKES SHIFT by Brinkley et al., Ser. No. 07/882,299, filed 5/13/92; and DETECTION USING MICROPARTICLES WITH CONTROLLABLE STOKES SHIFT, by Haugland et al., filed 5/20/94 (all three applications incorporated by reference), and methods known in the art.

The dibenzopyrromethenboron difluoride dye is covalently attached to the outer surface of the microparticle using any of the methods of conjugation described above. Dyes having an appropriate reactive functional group can be coupled covalently to amine-, thiol-, hydrazide-, epoxy- or carboxy-modified polymers. Alternatively, the reactive dyes are covalently incorporated within the microparticle after attachment and copolymerization according to known methods.

Figure 4:
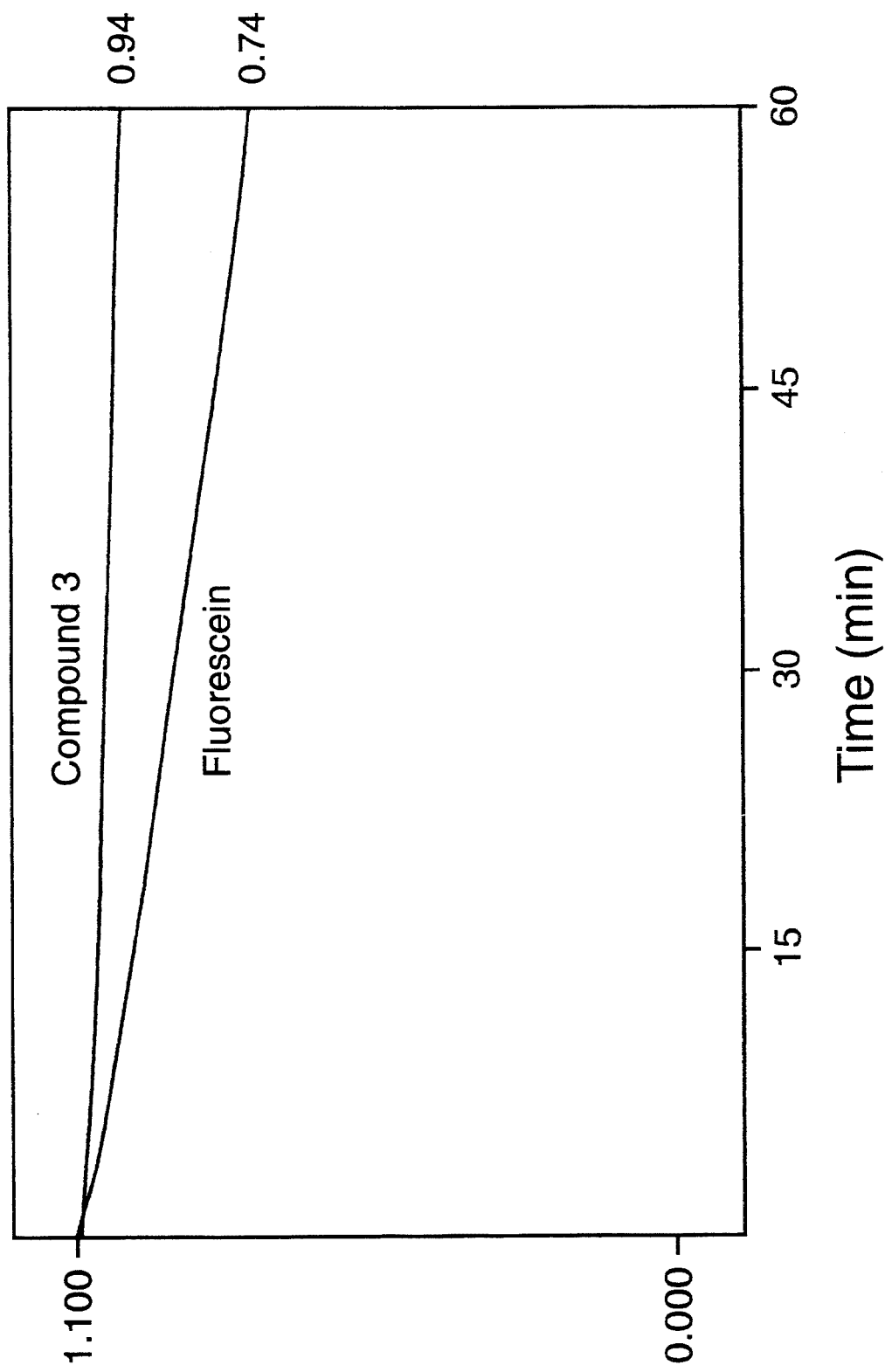

Suitably non-polar dyes of the invention are incorporated non-covalently within a polymer microparticle directly from an organic solution according to known methods. The neutral change and lipophilic character of most of the dibenzopyrromethenboron difluoride dyes facilitates their diffusion into and retention in nonpolar polymers such as polystyrene. Any polymer in which the dye is soluble at greater than about 0.01% by weight and from which the dye does not appreciably leach when brought into contact with water is suitable. One or more fluorescent dyes is incorporated into the microparticle from an organic solvent. The dyes are incorporated sequentially or as a mixture. Incorporation of multiple dyes with sufficient overlap between the absorption and emission peaks of the respective dyes, typically at a dye concentration of 1–5% by weight in the particle, results in effectively complete excited state energy transfer (Appl. Ser. No. 07/882,299, supra). For instance, in FIG. 4, a polymer microparticle containing multiple fluorescent dyes is illuminated at the wavelength of maximum output of an argon laser (488 nm). The longest-wavelength emitting dye in the microparticle of FIG. 4 is Compound 5 of the present invention. Although the absorption maximum for compound 5 is 673 nm, the excitation of the microparticle results in energy transfer from dye to dye, resulting in maximal fluorescence emission at the wavelength of Compound 5 (about 715 nm).

Usefully labeled microparticles contain an amount of fluorescent dye sufficient to make the microparticle fluorescent. The presence of too high a concentration of dye within a microparticle typically results in quenching of the fluorescence of the dye, and a decrease in the overall fluorescence response of the microparticle.

Microparticles labeled with fluorescent dyes either in their interior or on their surface are optionally surface modified with members of specific binding pairs such as peptides, proteins, antibodies, avidins, biotin, digoxigenin, haptens, nucleotides, oligonucleotides, nucleic acids, carbohydrates, lectins or enzymes according to methods known in the art. These modified and labeled microparticles are then allowed to interact with their complementary specific binding pair member for the purpose of detection or quantitation of that member or for attachment to other materials, including other members of specific binding pairs such as in amplification or layering techniques, or in creating a variety of probes. A variety of assays and means for detection of certain biological components are therefore possible using the dyes of the present invention.

The examples below are given so as to illustrate the practice of this invention. They are not intended to limit or define the entire scope of this invention.

EXAMPLES

Example 1

Preparation of 2-(1-naphthoyl)acetophenone

The following compound is prepared:

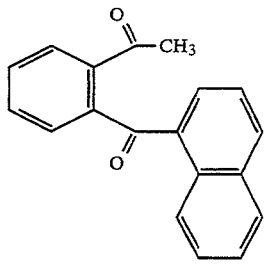

A solution of 5.0 g (26.5 mmol) of 1-naphthoylhydrazine and 5.5 g (40.0 mmol) of 2-hydroxyacetophenone in 30 mL of 1-propanol is heated under reflux overnight. After cooling to room temperature, the resulting solid is collected by filtration, washed with 1-propanol and dried to give 8.0 g (98%) of the N-naphthoylhydrazone of 2-hydroxyacetophenone. To a suspension of 2.5 g (8.0 mmol) of this hydrazone in 70 mL of tetrahydrofuran is added 4.3 g (9.7 mmol) of lead tetraacetate in small portions over a period of 10 minutes. After stirring at room temperature for 40 minutes, the resulting solid is removed by filtration. The filtrate is concentrated under vacuum and purified by silica gel chromatography using CHCl$_3$ as eluant, giving 2.1 g (92%) of the desired product.

Example 2

Preparation of 1-[[3(1-naphthyl)-2H-isoindol-1-yl]methylene]03-(1-naphthyl)-1-H-isoindole (1)

The following compound is prepared:

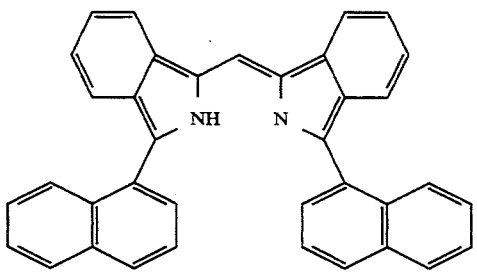

To a solution of 1.0 g (3.6 mmol) of 2-(1-naphthoyl)acetophenone in 50 mL of methanol and 25 mL of acetic acid is added 15 mL of concentrated NH$_4$OH. The mixture is stirred at room temperature for two days and the resulting solid is collected by filtration to give the crude product. The crude product is purified by silica gel chromatography with CHCl$_3$ as eluant to give 0.35 g (26%) of a dark blue solid.

Example 3

Preparation of difluoro[1-[[3-(1-naphthyl)-2-H-isoindol-1-yl]methylene]-3-(1-naphthyl)-1-H-isoindolato-N$^1$,N$^2$]boron (2)

The following compound is prepared:

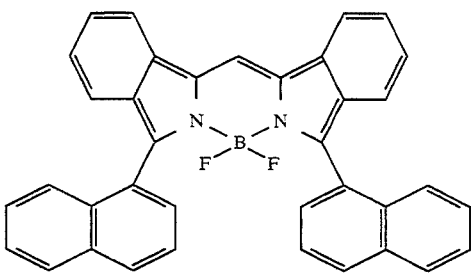

To a solution of 50 mg of 1 in 20 mL of CH$_2$Cl$_2$ is added 50 µL (0.29 mmol) of N,N-diisopropylethylamine, followed by addition of 35 µL (0.28 mmol) of BF$_3$.Et$_2$O. After the reaction mixture is stirred at room temperature for 3 hours, it is washed with two 20 mL portions of H$_2$O. The organic layer is separated, dried over anhydrous Na$_2$SO$_4$ and concentrated under reduced pressure to give a blue solid. The crude product is purified by chromatography on silica gel with CHCl$_3$ as eluant to give 20 mg (36%) of 2 as a dark blue solid.

Example 4

Preparation of difluoro[1-[(3-phenyl-2H-isoindol-1-yl)methylene]03-phenyl-1H-isoindolato-N$^1$,N$^2$]boron (3)

The following compound is prepared:

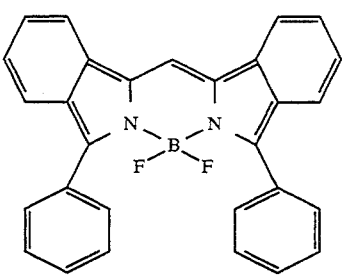

To a solution of 200 mg (0.50 mmol) of 1-[(3-phenyl-2H-isoindol-1-yl)methylene]-3-phenyl-1H-isoindole (prepared as described in Example 2 using 2-benzoacetophenone in place of 2(1-naphthoyl)acetophenone)) in 20 mL of CH$_2$Cl$_2$ is added 265 µL (1.52 mmol) of N,N-diisopropylethylamine, followed by addition of 180 µL (1.46 mmol) of BF$_3$.Et$_2$O. After the reaction mixture is stirred at room temperature for 12 hours, it is treated as described in Example 3 to give pure 3 as a dark blue solid (115 mg, 51%). mp. 275° C. dec. $^1$H NMR (DMSO-d$_6$) δ=7.32-7.37 (m, 2H, 2×ArH); 7.53-7.61 (m, 10H, 10×ArH); 7.73-7.76 (m, 4H, 4×ArH); 8.21 (d, 2H, 2×ArH); 8.72 (s, 1H, ArCH=).

Example 5

Preparation of 4-methoxy-2-(4-methoxybenzoyl)acetophenone

The following compound is prepared:

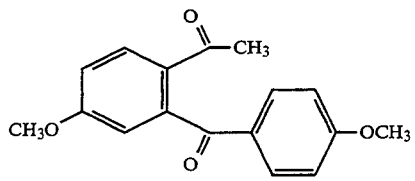

This precursor is prepared as described in Example 1, from 4-methoxybenzhydrazide (5.0 g, 30 mmol) and 2-hydroxy-4-methoxyacetophenone (5.0 g, 30 mmol). The desired compound (4.5 g, 68%) is obtained as a colorless solid.

Example 6

Preparation of 5-methoxy-1-[[5-methoxy-3-(4-methoxyphenyl)-2H-isoindol-1-yl]methylene-3-(4-methoxyphenyl)-1H-isoindole (4)

The following compound is prepared:

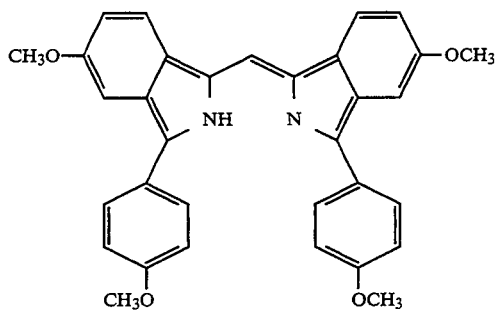

The product is prepared as described in Example 2 using 4-methoxy-2-(4-methoxybenzoyl)acetophenone (2.0 g, 7.0 mmol). Pure 4 is obtained as a dark blue solid (0.65 g, 18%).

Example 17

Preparation of difluoro[5-methoxy-1-[[5-methoxy-3-(4-methoxyphenyl)-2H-isoindol-1-yl]methylene]-3-(4-methoxyphenyl)-1H-isoindolato-$N^1,N^2$]boron (5)

The following compound is prepared:

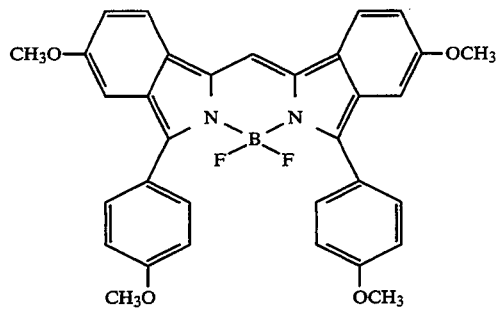

The product is prepared as described in Example 4 using 200 mg (0.39 mmol) of 4. Pure 5 is obtained as a dark blue solid (87 mg, 40%).

Example 8

Preparation of 2-(tert-butylcarbonyl)acetophenone

The following compound is prepared:

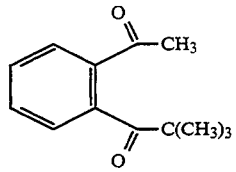

A solution of 15.0 g (130 mmol) of methyl trimethylacetate and 8 g (250 mmol) of hydrazine in 50 mL of CH$_3$OH is heated under reflux for 24 hours. After the reaction mixture is cooled to room temperature, the bulk of the CH$_3$OH is removed under reduced pressure. The residue is distilled under reduced pressure (15 mm Hg, 120° C.) to give trimethylacetic hydrazide (10 g, 75%), which slowly solidifies at room temperature.

The desired product is prepared as described in Example 1 using 2-hydroxyacetophenone (19.0 g, 140 mmol) and trimethylacetic hydrazide (10 g, 96 mmol). Yield: 5.0 g, 84%. m.p. 43°–45° C. $^1$H NMR (CDCl$_3$), δ=1.25 (s, 9H, 3×CH$_3$); 2.58 (s, 3H, CH$_3$); 7.21 (d, 1H, ArH); 7.45–7.49 (m, 1H, ArH); 7.55–7.59 (m, 1H, ArH); 7.89 (d, 1H, ArH).

Example 9

Preparation of 1-[[3-(t-butyl)-2H-isoindol-1-yl]methylene]-3-(t-butyl)-1H-isoindole (6)

The following compound is prepared:

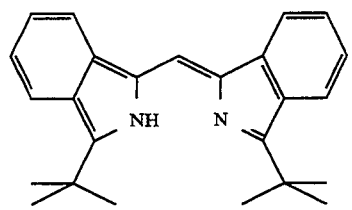

The product is prepared as described in Example 2 using 2-(t-butylcarbonyl)acetophenone. m.p. 195° C. $^1$H NMR (CDCl$_3$) δ=1.63 (s, 18H, 6×CH$_3$); 7.11–7.20 (m, 2H, 2×ArH); 7.23–7.31 (m, 2H, 2×ArH); 7.42 (s, 1H, ArCH=); 7.80–7.87 (m, 4H, 4×ArH).

Example 10

Preparation of difluoro[1-[[3-(t-butyl)-2H-isoindol-1-yl]methylene]-3-(t-butyl)-1H-isoindolato-$N^1,N^2$]boron (7)

The following compound is prepared:

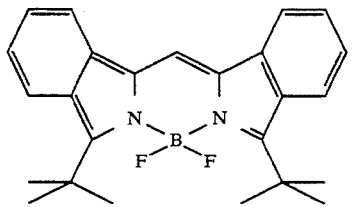

The product is prepared as described in Example 4 using 6 (40 mg, 0.11 mmol). As the product is unstable, 7 is obtained in solution only.

Example 11

Preparation of difluoro[1-[[3-(4-pyridyl)-2H-isoindol-1-yl]methylene]-3-(4-pyridyl)-1H-isoindolato-$N^1,N^2$]boron (8)

The following compound is prepared:

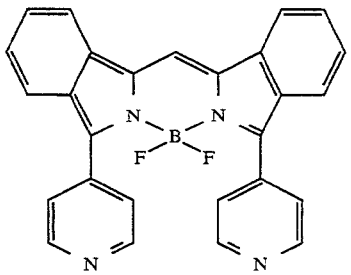

The product is prepared as described in Example 4 using 1[[3-(4-pyridyl)-2H-isoindol-1-yl]methylene]-3-(4-pyridyl)-1H-isoindole (200 mg, 0.50 mmol), which is prepared as described in Example 2 using 2-isonicotinoylacetophenone. Pure 8 is obtained as a dark blue solid (15 mg, 7%).

Example 12

Preparation of 1-benzoyl-2-acetonaphthone

The following compound is prepared:

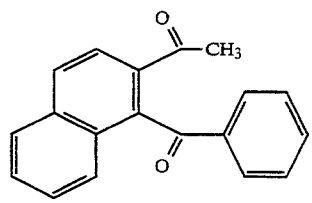

The product is prepared as described in Example 1, using 1-hydroxy-2-acetonaphthone (3.4 g, 18 mmol) and benzhydrazide (3.0 g, 22 mmol). The product is obtained as a colorless solid (4.0 g, 58%).

Example 13

Preparation of 1-[[3-phenyl-2H-benzo[c]isoindol-1-yl]methylene]-3-phenyl-1H-benzo[c]isoindole (9)

The following compound is prepared:

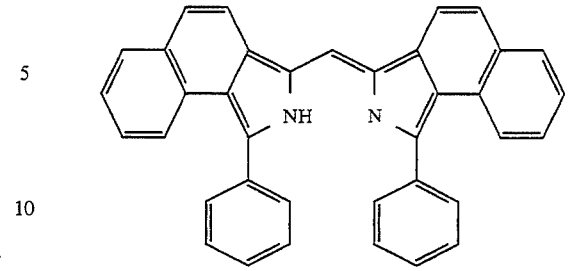

The product is prepared as described in Example 2 using 1-benzoyl-2-acetonaphthone (2.0 g, 7.3 mmol). Pure 9 is obtained as a dark blue solid (0.45 g, 16%).

Example 14

Preparation of difluoro[3-phenyl-1-[(3-phenyl-2H-benzo[c]isoindol-1-yl)methylene]-1H-benzo[c]isoindolato-$N^1,N^2$]boron (10)

The following compound is prepared:

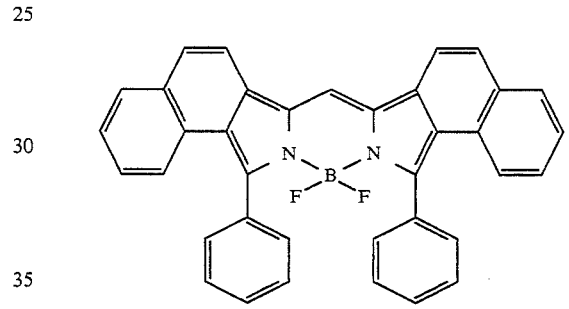

The product is prepared as described in Example 4 using 9 (100 mg, 0.2 mmol). Pure 10 is obtained as a dark blue solid (27 mg, 25%).

Example 15

Preparation of difluoro[1-[[3-(4-nitrophenyl)-2H-isoindol-1-yl]methylene]-03-(4-nitrophenyl)-1H-isoindolato-$N^1,N^2$]boron (11)

The following compound is prepared:

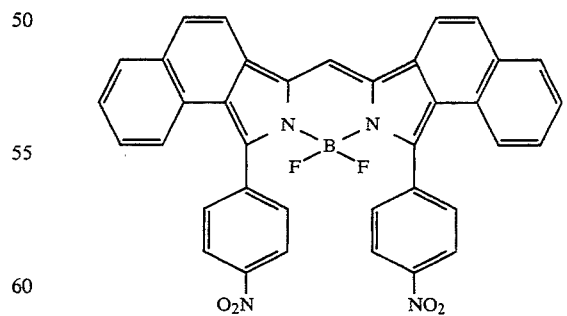

The product is prepared as described in Example 4 using 1-[[3-(4-nitrophenyl)-2H-isoindol-1-yl]methylene]-3-(4-nitrophenyl)-1H-isoindole (250 mg, 0.51 mmol), which is prepared as described in Example 2 using 2-(4-nitrobenzoyl)acetophenone. Pure 11 is obtained as a dark blue solid (32 mg, 12%).

Example 15

Preparation of difluoro[1-[[3-(4-isothiocyanatophenyl)-2H-isoindol-1-yl]methylene]-3-(4-isothiocyanatophenyl)-1H-isoindolato-$N^1,N^2$]boron (12)

The following compound is prepared:

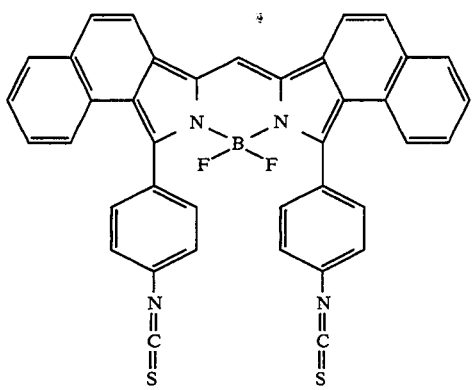

A mixture of 30 mg (0.06 mmol) of 11 and 70 mg (0.31 mmol) of $SnCl_2 \cdot 2H_2O$ in 5 mL of absolute EtOH is heated at 70° C. under nitrogen. After 30 minutes the reaction mixture is allowed to cool and the poured into an ice bath. The pH of the mixture is made slightly basic (pH 7–8) by addition of 5% aqueous $NaHCO_3$ before extraction with ethyl acetate. The organic layer is thoroughly washed with brine and dried over $Na_2SO_4$. Evaporation of the solvent gives 17 mg of a dark blue solid as a diamino compound. To a solution of the diamino compound in 5 mL of chloroform is added 20 μL of triethylamine, followed by the addition of 10 μL of thiophosgene and the mixture is stirred at room temperature for 1 hour. The mixture is then concentrated under reduced pressure and the resulting residue is purified by column chromatography on silica gel with $CHCl_3$ as eluant to give 22 mg (70%) of a dark blue solid as a diisothiocyanate.

Example 16

Labeling latex microparticles

To a stirred 100 mL suspension of carboxylate-modified latex (Interfacial Dynamics Corp. Portland, Ore.) that is 4.2% solids is added 50 mL methanol. A dye solution is prepared that is 25–50 mg desired dye(s), 7.5 mL methylene chloride and 17.5 mL ethanol. As vigorous stirring is continued, the dye solution is added to the latex suspension. The addition of the dye(s) is carried out by means of a syringe pump fitted with a Teflon delivery tube and the dye solution is delivered at a low flow rate (~6 mL/hr). After addition is complete, the organic solvents are evaporated at room temperature on a rotary evaporator. The aqueous suspension of dyed latex is then filtered through glass wool to remove any additional debris and dialyzed in E-pure water (25 mm tubing, MW cutoff 12,000–14,000) to remove any residual dye. The dialysis is carried out until no more free dye is removed from the particles as detected by fluorimetric analysis of the dialysate. The fluorescent latex suspension is removed from dialysis and filtered again through glass wool to remove any remaining aggregates and other debris. The suspension is then sonicated in a bath sonicator for 5 minutes to ensure monodispersity. Visual or instrumental analysis of a dilute aqueous suspension of the product by fluorescence microscopy using standard filters shows uniformly dyed particles that are highly monodisperse.

It is to be understood that, while the foregoing invention has been described in detail by way of illustration and example, numerous modifications, substitutions, and alterations are possible without departing from the spirit and scope of the invention as described in the following claims.

What is claimed is:

1. A compound of the formula:

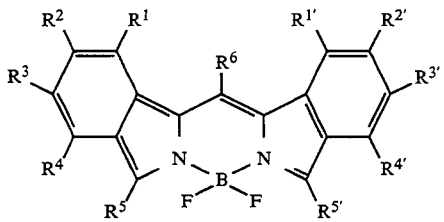

wherein $R^1$, $R^2$, $R^3$, $R^4$, $R^{1'}$, $R^{2'}$, $R^{3'}$, and $R^{4'}$ are optionally and independently H, halogen, cyano, sulfo, alkali or ammonium salts of sulfo, carboxy, alkyl, perfluoroalkyl, alkoxy, alkylthio, nitro, amino, monoalkylamino, dialkylamino, alkylamido; or substituted or unsubstituted ARYL, ARYL-oxy, HETEROARYL, HETEROARYL-oxy, ARYL-amino, HETEROARYL-amino, ARYL-amido or HETEROARYL-amido; or two adjacent substituents are fused to form BENZO or HETERO;

wherein

BENZO is $-CR^7=CR^8-CR^9=CR^{10}-$ bonded to any two adjacent positions of $R^1$, $R^2$, $R^3$, $R^4$, $R^{1'}$, $R^{2'}$, $R^{3'}$, and $R^{4'}$, up to a maximum of four BENZO moieties;

$R^7$, $R^8$, $R^9$ and $R^{10}$ are independently selected from H, halogen, cyano, sulfo, alkali or ammonium salts of sulfo, carboxy, alkyl, perfluoroalkyl, alkoxy, alkylthio, nitro, amino, monoalkylamino, dialkylamino, alkylamido;

HETERO is a combination of 1 to 3 carbon atoms and 1 to 3 hetero atoms selected from the group consisting of O, S and N to form a fused 5- or 6-membered heteroaromatic ring bonded to any two adjacent positions of $R^1$, $R^2$, $R^3$, $R^4$, $R^{1'}$, $R^{2'}$, $R^{3'}$ that is optionally and independently substituted by H, halogen, cyano, sulfo, alkali or ammonium salt of sulfo, carboxy, alkyl, perfluoroalkyl, alkoxy, alkylthio, amino, monoalkylamino, dialkylamino or alkylamido;

ARYL is an aromatic or polyaromatic substituent containing 1 to 4 aromatic rings having 6 conjugated carbon atoms and no heteroatoms that are optionally fused to each other or bonded to each other by carbon-carbon single bonds and attached by a single bond, and is optionally and independently substituted by H, halogen, cyano, sulfo, alkali or ammonium salt of sulfo, carboxy, nitro, alkyl, perfluoroalkyl, alkoxy, alkylthio, amino, monoalkylamino, dialkylamino or alkylamido;

HETEROARYL is a 5- or 6-membered aromatic heterocycle that is optionally fused to additional six-membered aromatic rings, or is fused to one 5- or 6-membered heteroaromatic ring, said heteroaromatic rings contain at least 1 and as many as 3 heteroatoms that are selected from the group consisting of O, N or S in any combination and HETEROARYL is attached by a single bond, and is optionally and independently substituted by H, halogen, cyano, sulfo, alkali or ammonium salt or sulfo, carboxy, alkyl, perfluoroalkyl, alkoxy, alkylthio, amino, monoalkylamino, dialklamino or alkylamido;

$R^5$ and $R^{5'}$ are independently alkyl, cycloalkyl having 3–6 carbons, perfluoroalkyl, ARYL or HETEROARYL;

$R^6$ is H, alkyl, cycloalkyl having 3–6 carbons, perfluoroalkyl, ARYL or HETEROARYL;

all alkyl and perfluoro groups have 1–18 carbon atoms in an arrangement that is either linear or branched; and all alkyl substituents and alkyl portions of substituents are optionally further substituted by H, halogen, cyano, amino, hydroxy, carboxy, mercapto, sulfo, or alkali or ammonium salt of sulfo.

2. A compound as claimed in claim 1, wherein $R^1=R^{1'}$, $R^2=R^{2'}$, $R^3=R^{3'}$, $R^4=R^{4'}$ and $R^5=R^{5'}$.

3. A compound as claimed in claim 1, wherein at least one of $R^1$ with $R^2$ and $R^{1'}$ with $R^{2'}$ are —$CR^7$=$CR^8$—$CR^9$=$CR^{10}$—.

4. A compound as claimed in claim 1, wherein at least one of $R^3$ with $R^4$ and $R^{3'}$ with $R^{4'}$ are —$CR^7$=$CR^8$—$CR^9$=$CR^{10}$—.

5. A compound as claimed in claim 1, wherein at least one of $R^5$ and $R^{5'}$ is HETEROARYL.

6. A compound as claimed in claim 1, wherein at least one of $R^5$ and $R^{5'60}$ is ARYL.

7. A compound as claimed in claim 6, wherein ARYL is phenyl, substituted phenyl, naphthyl or substituted naphthyl.

8. A compound as claimed in claim 1, wherein at least one of $R^1$, $R^2$, $R^3$, $R^4$, $R^{1'}$, $R^{2'}$, $R^{3'}$ or $R^{4'}$ is an alkyl, alkoxy, alkylthio, monoalkylamino, dialkylamino or alkylamido group that is optionally substituted by halogen, amino, hydroxy, cyano, carboxy, mercapto, sulfo, or alkali or ammonium salt of sulfo; or one of the substituents at $R^1$, $R^2$, $R^3$, $R^4$, $R^{1'}$, $R^{2'}$, $R^{3'}$ or $R^{4'}$ is sulfo, alkali or ammonium salt of sulfo, carboxy or amino.

9. A compound as claimed in claim 1, wherein at least one of $R^5$, $R^{5'}$ or $R^6$ is ARYL, ARYL-oxy, HETEROARYL, HETEROARYL-oxy, ARYL-amino or HETEROARYL-amino that is further substituted by alkyl, alkoxy, alkylthio, monoalkylamino, dialkylamino, alkylamido, halogen, amido, hydroxy, cyano, carboxy, mercapto, sulfo, alkali or ammonium salt of sulfo.

10. A fluorescent dye of the formula:

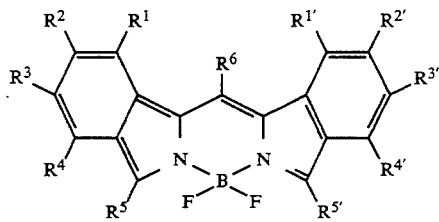

wherein $R^1$, $R^2$, $R^3$, $R^4$, $R^{1'}$, $R^{2'}$, $R^{3'}$, and $R^{4'}$ are optionally and independently H, halogen, cyano, sulfo, alkali or ammonium salts of sulfo, carboxy, alkyl, perfluoroalkyl, alkoxy, alkylthio, nitro, amino, monoalkylamino, dialkylamino, alkylamido; or substituted or unsubstituted ARYL, ARYL-oxy, HETEROARYL, HETEROARYL-oxy, ARYL-amino, HETEROARYL-amino, ARYL-amido or HETEROARYL-amido; or two adjacent substituents are fused to form BENZO;

wherein

BENZO is —$CR^7$=$CR^8$—$CR^9$=$CR^{10}$— bonded to any two adjacent positions of $R^1$, $R^2$, $R^3$, $R^4$, $R^{1'}$, $R^{2'}$, $R^{3'}$, and $R^{4'}$, up to a maximum of four BENZO moieties;

$R^7$, $R^8$, $R^9$ and $R^{10}$ are independently selected from H, halogen, cyano, sulfo, alkali or ammonium salts of sulfo, carboxy, alkyl, perfluoroalkyl, alkoxy, alkylthio, nitro, amino, monoalkylamino, dialkylamino, alkylamido;

ARYL is an aromatic or polyaromatic substituent containing 1 to 4 aromatic rings having 6 conjugated carbon atoms and no heteroatoms that are optionally fused to each other or bonded to each other by carbon-carbon single bonds and attached by a single bond, and is optionally and independently substituted by H, halogen, cyano, sulfo, alkali or ammonium salt of sulfo, carboxy, nitro, alkyl, perfluoroalkyl, alkoxy, alkylthio, amino, monoalkylamino, dialkylamino or alkylamido;

HETEROARYL is a 5- or 6-membered aromatic heterocycle that is optionally fused to additional six-membered aromatic rings, or is fused to one 5- or 6-membered heteroaromatic ring, said heteroaromatic rings contain at least 1 and as many as 3 heteroatoms that are selected from the group consisting of O, N or S in any combination and HETEROARYL is attached by a single bond, and is optionally and independently substituted by H, halogen, cyano, sulfo, alkali or ammonium salt or sulfo, carboxy, alkyl, perfluoroalkyl, alkoxy, alkylthio, amino, monoalkylamino, dialklamino or alkylamido;

$R^5$ and $R^{5'}$ are independently alkyl, cycloalkyl having 3–6 carbons, perfluoroalkyl, ARYL or HETEROARYL;

$R^6$ is H, alkyl, cycloalkyl having 3–6 carbons, perfluoroalkyl, ARYL or HETEROARYL;

all alkyl and perfluoro groups have 1–18 carbon atoms in an arrangement that is either linear or branched;

all alkyl substituents and alkyl portions of substituents are optionally further substituted by H, halogen, cyano, amino, hydroxy, carboxy, mercapto, sulfo, or alkali or ammonium salt of sulfo;

wherein such dye is further modified such that at least one substituent contains an amino, an isocyanate, a dichloro-1,3,5-triazine, a maleimide, a haloacetamide, a carboxy, an anhydride, an acid halide, an acyl azide, an acyl hydrazide, an activated ester, a sulfo, a sulfonyl chloride, a sulfonyl fluoride, an alcohol, an alkylating agent, a thiol, or a disulfide group; or said compound is covalently attached to a conjugant.

11. A fluorescent dye, as claimed in claim 10, wherein $R^1=R^{1'}$, $R^2=R^{2'}$, $R^3=R^{3'}$, $R^4=R^{4'}$ and $R^5=R^{5'}$.

12. A fluorescent dye, as claimed in claim 10, wherein said dye contains at least one amino, carboxy, sulfo, alcohol or thiol group.

13. A fluorescent dye, as claimed in claim 10, wherein said dye is covalently attached to a conjugant.

14. A fluorescent composition, comprising:
a fluorescent dye of the formula:

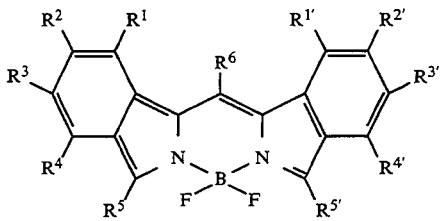

wherein
R$^1$, R$^2$, R$^3$, R$^4$, R$^{1'}$, R$^{2'}$, R$^{3'}$, and R$^{4'}$ are optionally and independently H, halogen, cyano, sulfo, alkali or ammonium salts of sulfo, carboxy, alkyl, perfluoroalkyl, alkoxy, alkylthio, nitro, amino, monoalkylamino, dialkylamino, alkylamido, or substituted or unsubstituted ARYL, ARYL-oxy, HETEROARYL, HETEROARYL-oxy, ARYL-amino, HETEROARYL-amino, ARYL-amido or HETEROARYL-amido; or two adjacent substituents are fused to form BENZO or HETERO;
wherein
BENZO is —CR$^7$=CR$^8$—CR$^9$=CR$^{10}$— bonded to any two adjacent positions of R$^1$, R$^2$, R$^3$, R$^4$, R$^{1'}$, R$^{2'}$, R$^{3'}$, and R$^{4'}$, up to a maximum of four BENZO moieties;
R$^7$, R$^8$, R$^9$ and R$^{10}$ are independently selected from H, halogen, cyano, sulfo, alkali or ammonium salts of sulfo, carboxy, alkyl, perfluoroalkyl, alkoxy, alkylthio, nitro, amino, monoalkylamino, dialkylamino, alkylamido;
HETERO is a combination of 1 to 3 carbon atoms and 1 to 3 hetero atoms selected from the group consisting of O, S and N to form a fused 5- or 6-membered heteroaromatic ring bonded to any two adjacent positions of R$^1$, R$^2$, R$^3$, R$^4$, R$^{1'}$, R$^{2'}$, R$^{3'}$ that is optionally and independently substituted by H, halogen, cyano, sulfo, alkali or ammonium salt of sulfo, carboxy, alkyl, perfluoroalkyl, alkoxy, alkylthio, amino, monoalkylamino, dialkylamino or alkylamido;
ARYL is an aromatic or polyaromatic substituent containing 1 to 4 aromatic rings having 6 conjugated carbon atoms and no heteroatoms that are optionally fused to each other or bonded to each other by carbon-carbon single bonds and attached by a single bond, and is optionally and independently substituted by H, halogen, cyano, sulfo, alkali or ammonium salt of sulfo, carboxy, nitro, alkyl, perfluoroalkyl, alkoxy, alkylthio, amino, monoalkylamino, dialkylamino or alkylamido;
HETEROARYL is a 5- or 6-membered aromatic heterocycle that is optionally fused to additional six-membered aromatic rings, or is fused to one 5- or 6-membered heteroaromatic ring, said heteroaromatic rings contain at least 1 and as many as 3 heteroatoms that are selected from the group consisting of O, N or S in any combination and HETEROARYL is attached by a single bond, and is optionally and independently substituted by H, halogen, cyano, sulfo, alkali or ammonium salt or sulfo, carboxy, alkyl, perfluoroalkyl, alkoxy, alkylthio, amino, monoalkylamino, dialklamino or alkylamido;

R$^5$ and R$^{5'}$ are independently alkyl, cycloalkyl having 3–6 carbons, perfluoroalkyl, ARYL or HETEROARYL;

R$^6$ is H, alkyl, cycloalkyl having 3–6 carbons, perfluoroalkyl, ARYL or HETEROARYL;
all alkyl and perfluoro groups have 1–18 carbon atoms in an arrangement that is either linear or branched;
all alkyl substituents and alkyl portions of substituents are optionally further substituted by H, halogen, cyano, amino, hydroxy, carboxy, mercapto, sulfo, or alkali or ammonium salt of sulfo;
associated with a polymeric microparticle, in an amount sufficient to make said microparticle fluorescent.

15. A fluorescent composition, as claimed in claim 14, wherein said polymeric microparticle comprises polystyrene, brominated polystyrene, nitrocellulose, polyacrylic acid, polyacrylonitrile, polyacrylamide, polyacrolein, polydimethylsiloxane, polybutadiene, polyisoprene, polyurethane, polyvinylacetate, polyvinylchloride, polyvinylpyridine, polyvinylbenzylchloride, polyvinyltoluene, polyvinylidene chloride, or polydivinylbenzene.

16. A fluorescent composition, as claimed in claim 14, wherein said fluorescent dye is incorporated non-covalently within said microparticle.

17. A fluorescent composition, as claimed in claim 14, wherein said fluorescent dye is covalently attached to the surface of said microparticle.

18. A fluorescent composition, as claimed in claim 14, wherein said fluorescent composition further comprises a member of a specific binding pair.

19. A fluorescent composition, as claimed in claim 18, wherein said specific binding pair member is a peptide, protein, nucleotide, oligonucleotide, carbohydrate or hapten.

20. A fluorescent composition, as claimed in claim 18, wherein said specific binding pair member is avidin, streptavidin, biotin, or digoxigenin.

21. A fluorescent composition, as claimed in claim 14, further comprising 1–4 additional different fluorescent dyes.

22. A compound, as claimed in claim 1, wherein R$^1$, R$^2$, R$^3$, R$^4$, R$^{1'}$, R$^{2'}$, R$^{3'}$, and R$^{4'}$ are optionally and independently H, alkoxy, or two adjacent substituents are fused to form BENZO; R$^6$ is H; R$^7$, R$^8$, R$^9$ and R$^{10}$ are H; R$^5$ and R$^{5'60}$ are alkyl having 3–6 carbons, ARYL or HETEROARYL;
wherein
ARYL is phenyl; and
HETEROARYL is thienyl, pyrrolyl or pyridyl.

23. A compound, as claimed in claim 8, wherein one of the substituents at R$^1$, R$^2$, R$^3$, R$^4$, R$^{1'}$, R$^{2'}$, R$^{3'}$ or R$^{4'}$ is sulfo, alkali or ammonium salt of sulfo, carboxy or amino.

24. A fluorescent dye, as claimed in claim 10, wherein said dye contains exactly one amino, isocyanate, dichloro-1,3,5-triazine, maleimide, haloacetamide, carboxy, anhydride, acid halide, acyl azide, acyl hydrazide activated ester, sulfo, sulfonyl chloride, sulfonyl fluoride, alcohol, alkylating agent, thiol, thioester, or disulfide group.

25. A fluorescent dye, as claimed in claim 10, wherein said dye contains an isocyanate, isothiocyanate, 4,6-dichloro-1,3,5-triazine, maleimide, or haloacetamide.

26. A fluorescent dye, as claimed in claim 10, wherein said dye contains an anhydride, acid halide, acyl azide, acyl hydrazide, or an activated ester that is a succinimidyl ester, p-nitrophenyl ester, or a pentafluorophenyl ester.

27. A fluorescent dye, as claimed in claim 10, wherein said dye contains a sulfonyl chloride or a sulfonyl fluoride.

28. A fluorescent dye, as claimed in claim 13, wherein said conjugant is an antibody, streptavidin, a nucleotide, an oligonucleotide, or a natural or synthetic drug.

29. A fluorescent composition, as claimed in claim 14, wherein $R^1$, $R^2$, $R^3$, $R^4$, $R^{1'}$, $R^{2'}$, $R^{3'}$, and $R^{4'}$ are optionally and independently H, alkoxy, or two adjacent substituents are fused to form BENZO; $R^6$ is H; $R^7$, $R^8$, $R^9$ and $R^{10}$ are H; $R^5$ and $R^{5'}$ are alkyl having 3–6 carbons, ARYL or HETEROARYL;
wherein
ARYL is phenyl; and
HETEROARYL is thienyl, pyrrolyl or pyridyl.

30. A compound, as claimed in claim 1, having the structure

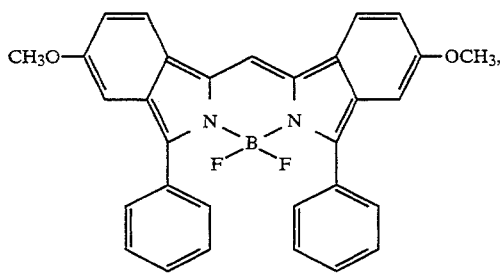

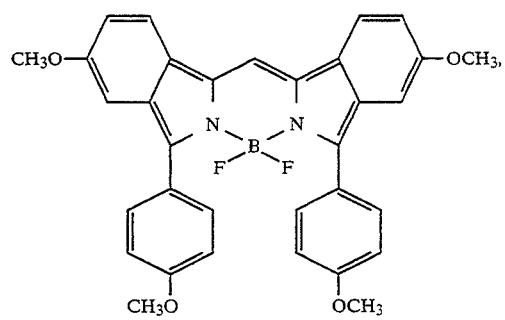

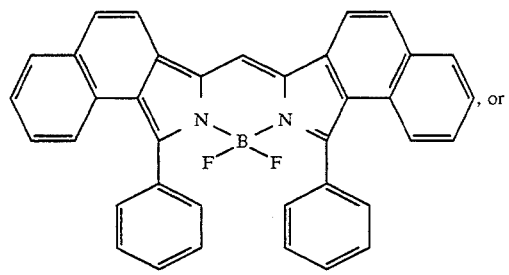

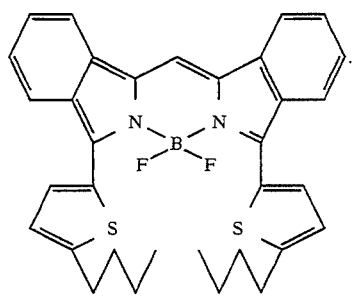

* * * * *

UNITED STATES PATENT AND TRADEMARK OFFICE
CERTIFICATE OF CORRECTION

PATENT NO. : 5,433,896
DATED : July 18, 1995
INVENTOR(S) : Kang et al.

It is certified that error appears in the above-indentified patent and that said Letters Patent is hereby corrected as shown below:

At Col. 1, line 51, "5,178,288" should be --5,187,288--

At Col. 3, line 57, "(C'O)" should be --(C=O)--

At Col. 5, line 1, "2-pyrrolyl, 2-oxazolyl" should be --2-pyrrolyl, 2-indolyl, 2-oxaxolyl--

At Col. 7, line 61, insert heading --SYNTHESIS--

At Col. 9, line 30, "(C'O)" should be --(C=O)--

At Col.11, line 31, "dibenzopyrrometheneboron" should be --dipyrrometheneboron--

At Col.13, Table 2, footnote ‡ "( )" should be --(Ø)--; "( =0.25)" should be --(Ø=0.25)--; and "( =0.54)" should be --(Ø=0.54)--.

At Col.13, line 67, "( )" should be --(Ø)--; "( =0.25)" should be --(Ø=0.25)--.

At Col.18, lines 57 "2-benzoacetophenone" should be --2-benzoylacetophenone--

At Col.19, line 47, "Example 17" should be --Example 7--.

UNITED STATES PATENT AND TRADEMARK OFFICE
CERTIFICATE OF CORRECTION

PATENT NO. : 5,433,896
DATED : July 18, 1995
INVENTOR(S) : Kang et. al

It is certified that error appears in the above-indentified patent and that said Letters Patent is hereby corrected as shown below:

At Col. 22, lines 1-13, the structure should appear as follows:

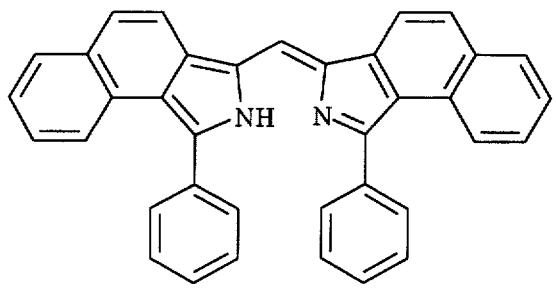

At Col. 22, lines 25-36, the structure should appear as follows:

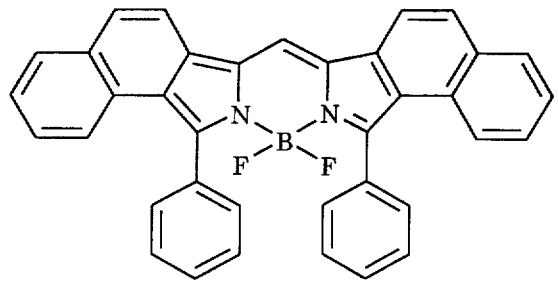

UNITED STATES PATENT AND TRADEMARK OFFICE
CERTIFICATE OF CORRECTION

PATENT NO.    : 5,433,896
DATED         : July 18, 1995
INVENTOR(S)   : Kang et. al It is certified that error appears in the above-indentified patent and that said Letters Patent is hereby corrected as shown below:

At Col. 22, lines 50-62, the structure should appear as follows:

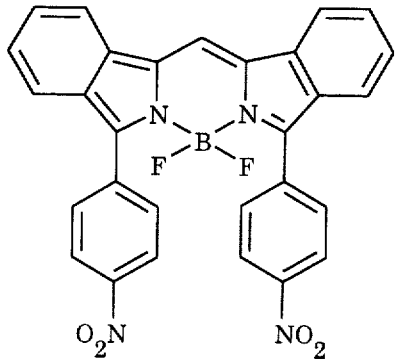

At Col. 23, lines 8-24, the structure should appear as follows:

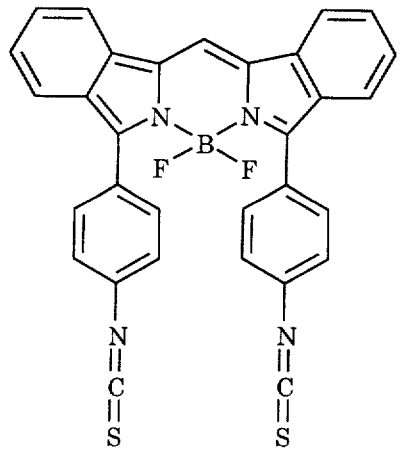

UNITED STATES PATENT AND TRADEMARK OFFICE
CERTIFICATE OF CORRECTION

PATENT NO. : 5,433,896
DATED : July 18, 1995
INVENTOR(S) : Kang et. al

It is certified that error appears in the above-indentified patent and that said Letters Patent is hereby corrected as shown below:

At Col. 24, lines 49-50, "$R^{1\prime}$, $R^{2\prime}$, $R^{3\prime}$, that is" should be --$R^{1\prime}$, $R^{2\prime}$, $R^{3\prime}$, and $R^{4\prime}$ that is--

At Col. 26, line 42, "dialklamino" should be --dialkylamino--.

At Col. 27, lines 41-42, "$R^{1\prime}$, $R^{2\prime}$, $R^{3\prime}$, that is" should be --$R^{1\prime}$, $R^{2\prime}$, $R^{3\prime}$, and $R^{4\prime}$ that is--

At Col. 28, line 2, "dialklamino" should be --dialkylamino--.

At Col. 28, line 50, "$R^{5\prime 60}$" should be --$R^{5\prime}$--.

Signed and Sealed this

Twenty-fifth Day of August, 1998

Attest:

BRUCE LEHMAN

*Attesting Officer*                    *Commissioner of Patents and Trademarks*